United States Patent [19]

Herskovitz et al.

[11] 4,357,136
[45] Nov. 2, 1982

[54] METHOD FOR FILLING A ROOT CANAL

[75] Inventors: Sheldon B. Herskovitz, Acton; Jay Marlin, Leominster; Martin R. Stiglitz, Lexington, all of Mass.

[73] Assignee: Solar Energy Technology, Inc., Bedford, Mass.

[21] Appl. No.: 260,038

[22] Filed: May 4, 1981

Related U.S. Application Data

[62] Division of Ser. No. 831,714, Sep. 9, 1977, Pat. No. 4,265,618.

[51] Int. Cl.³ .............................................. A61C 5/02
[52] U.S. Cl. .................................................... 433/224
[58] Field of Search ........................... 433/224, 32, 81

[56] References Cited

U.S. PATENT DOCUMENTS

| | | | |
|---|---|---|---|
| 944,254 | 12/1909 | Binford | 433/226 |
| 1,140,660 | 5/1915 | Brizius | 433/32 |
| 1,189,735 | 7/1916 | Quintin | 433/81 |
| 1,619,817 | 3/1927 | Gibson | 433/32 |
| 2,505,028 | 4/1950 | Boeger | 128/215 |
| 3,154,811 | 11/1964 | Gardener | 219/241 |
| 3,466,752 | 9/1969 | Braun | 433/90 |
| 4,121,587 | 10/1978 | Kronman et al. | 128/236 |
| 4,122,850 | 10/1978 | Bucalo | 128/216 |

FOREIGN PATENT DOCUMENTS 1120779  7/1956  France ............................... 433/226

OTHER PUBLICATIONS

"Three-Dimensional Obturation of the Root Canal Using Injection Molded, Thermoplasticized Dental Gutta-Percha", by F. S. Yee et al., Journal of Endodontics, vol. 3, No. 5, May 1977, pp. 168-174.

*Primary Examiner*—Gene Mancene
*Assistant Examiner*—John J. Wilson
*Attorney, Agent, or Firm*—Hamilton, Brook, Smith & Reynolds

[57] ABSTRACT

A syringe for extruding heated thermoplastic materials through a hollow needle is disclosed. This syringe is particularly useful in obturating root canal cavities, or other dental cavities, with gutta-percha or similar materials.

1 Claim, 4 Drawing Figures

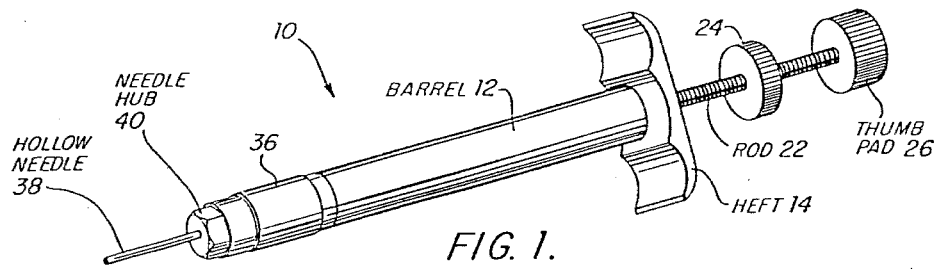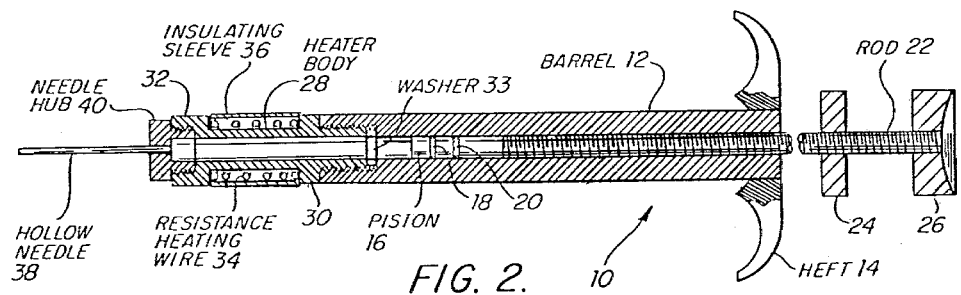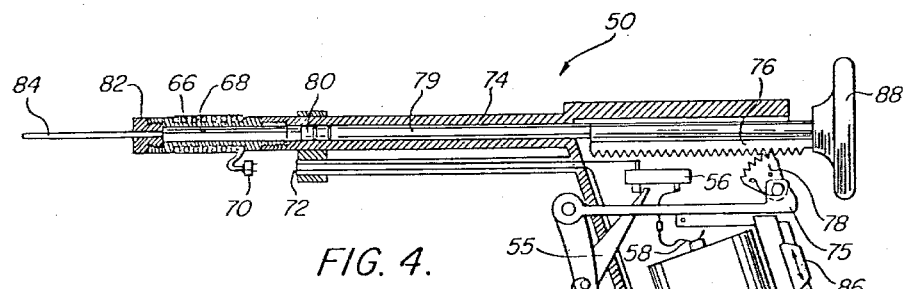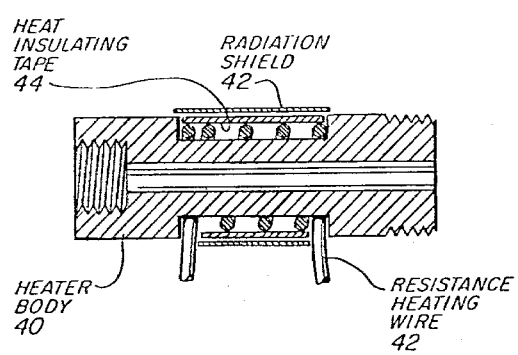

METHOD FOR FILLING A ROOT CANAL

This application is a division of application Ser. No. 831,714, filed Sept. 9, 1977 now U.S. Pat. No. 4,265,618, May 5, 1981.

BACKGROUND OF THE INVENTION

1. Field of the Invention

This invention is in the field of syringes and more particularly relates to syringes adapted for extruding heated thermoplastic materials through a hollow needle.

2. Description of the Prior Art

Presently, root canal cavities as well as other dental cavities are obturated by filling them with heated gutta-percha. Gutta-percha is a purified, coagulated, milkly exudate obtained from certain species of trees, and is defined as a trans isomer of rubber. It becomes plastic at about 140° F., and will flow through hollow needles of the type used in dental syringes at around 230° F.

The method most commonly employed for filling dental cavities with gutta-percha is to apply small amounts of heated gutta-percha into the cavity with a hot probe and to compact the material within the cavity using a condensor. This is a very time consuming and tedious process, at best, however, and may, in some cases, not result in complete filling and sealing of the dental cavity.

Recently, it has been recognized that the application of injection molding principles to obturate root canal cavities with gutta-percha offers great promise. It has been demonstrated, for example, by researchers in the field of endodontics that gutta-percha can be used to obturate root canal cavities using injection molding principles. See Yee, F. S., Marlin J., Krakow, A. P., and Gron, P.; "Three-Dimensional Obturation of the Root Canal Using Injection-Molded, Thermoplasticized Dental Gutta-Percha"; *J. Endodontics*, 3; No. 5; May, 1977; pp. 168-174. These experiments were performed in vitro, but their application in vivo would seem possible if suitable equipment were available. In addition to achieving outstanding sealing of the cavities, the techniques seem to offer potential advantages in their simplicity, reduction in time by skilled personnel, and reduction in the amount of manipulative procedures necessary for condensation of gutta-percha. Despite such promise, these techniques have not been widely accepted due to the lack of suitable equipment, such as dental syringes, for carrying out such techniques.

There have been hypodermic needles and tools which have heated tips, of course. For example, Piper et al., in U.S. Pat. No. 3,698,394, disclose a surgical hypodermic needle wherein the tip of the needle is heated with an electric current passed through resistance wires within the needle adjacent to its tip. This needle is used to destroy blood vessels or tissues. Clearly, such a needle would be unsuitable for filling dental cavities, such as those formed in root canal work, since the heating wires and insulation surrounding the needle make it so bulky that it would be difficult to insert and manipulate into a root canal cavity.

Malisza, in U.S. Pat. No. 3,614,389, discloses an electrically heated temperature control waxing apparatus for use in making wax models for dental purposes. However, this apparatus does not include an elongated hollow needle of the type necessary to insert into root canal cavities. In fact, the problem of supplying sufficient heat to a small diameter hollow needle so that its entire length, including its tip, stays above the temperature at which the material being extruded is plastic is very difficult in view of the convection losses which occur along the needle. In applications such as obturation of root canal cavities, the needle requires a minimum length, often one inch or more, and it is difficult to maintain the required temperature along the entire length of such needles.

Thus, despite great promise, injection molding principles have not been widely accepted by the dental profession for obturating root canal cavities. This is principally due to the lack of adequate equipment for applying such principles to this problem.

SUMMARY OF THE INVENTION

This invention relates to a syringe which is uniquely designed to allow the extrusion of heated thermoplastic materials through hollow needles.

This syringe has a chamber means for holding a supply of thermoplastic material, such as a relatively elongated, hollow, syringe barrel. A hollow needle through which the thermoplastic material is to be ejected is fabricated from a material having a relatively high thermal conductivity which insures that sufficient heat flows along the needle to maintain it at a temperature above the point at which the thermoplastic material will flow, despite convection or other losses. The needle is joined to the chamber means by suitable means for joining such as a needle hub. Preferably, the needle hub is also fabricated from a material having high thermal conductivity. Means for advancing the thermoplastic material from the chamber means through the hollow needle are provided, and commonly are a piston located within the hollow syringe barrel. Finally, means for heating the thermoplastic material and needle to temperatures sufficient to allow the thermoplastic material to flow through the needle are provided. Such means may be, for example, a separate heater section inserted in the assembly between the needle hub and syringe cylinder. A suitable heater can be formed from a hollow tube fabricated from material having a relatively high thermal conductivity and wrapped with electrical resistance heating wires over which thermal insulation is provided.

The syringe of this invention allows the outstanding promise offered by injection molding techniques to be realized in obturating dental cavities with gutta-percha or other thermoplastic materials. Such promise is realized because the syringe is uniquely designed to maintain the needle at a temperature above the plastic point of the thermoplastic material along its entire length to insure that the thermoplastic material is maintained and extruded in a plastic state. Because of this, the thermoplastic material flows within the dental cavity and conforms to the dimensions of the cavity insuring that outstanding obturation is obtained.

Additionally, this syringe has self-contained heating elements and does not depend upon an external source of heat, such as the hot baths sometimes employed in prior attempts to heat syringes. These self-contained heating elements are sufficient, however, to rapidly heat the thermoplastic material to a temperature above its plastic point which reduces the amount of time required to complete introduction of the material into the cavity. Such rapid heating is possible because of the outstanding thermal paths provided by the design described herein. Since the self-contained heating elements may be powered by a source also located within the syringe, there is also great flexibility in designing portable syringe models.

The syringe of this invention is also constructed so that it can be held without any requirement for special heat-insulating gloves, etc. Such heat-insulating gloves are, of course, cumbersome and tend to interfere with the freedom of movement which is necessary to obturating root canal cavities.

Thus, root canal cavities, or other dental cavities, can be filled efficaciously, easily and quickly by employing syringes according to this invention and this has not been possible heretofor.

BRIEF DESCRIPTION OF THE DRAWINGS

FIG. 1 is a perspective view illustrating one embodiment of a syringe according to this invention;

FIG. 2 is a cross-sectional view illustrating each of the components in the syringe of FIG. 1;

FIG. 3 is a cross-sectional view illustrating one internal heater design suitable for syringes of this invention; and, FIG. 4 is a cut-away side elevation view illustrating an alternative embodiment of a syringe according to this invention which is trigger operated.

DESCRIPTION OF PREFERRED EMBODIMENTS

The invention will now be described further by reference to the Figures in more detail.

FIGS. 1 and 2 illustrate one embodiment of a hand-operable syringe 10 according to this invention. Syringe 10 has a hollow cylinder or barrel 12 which is capable of holding an internal supply of thermoplastic material. Heft 14 is attached to barrel 12 to facilitate handling and operation of syringe 10.

Piston 16 is slidably engaged within barrel 12 and serves to advance thermoplastic material through barrel 12. Piston 16 haw two narrow grooves, 18 and 20, cut into its outer surface and extending around its entire periphery. Grooves 18 and 20 serve to catch and trap heated thermoplastic material flowing in the reverse direction, and act, therefore, as seals.

Elongated rod 22 is integrally attached to piston 16 and has a threaded portion extending from barrel 12 and beyond heft 14. A circular, internally threaded nut 24 is mounted on threaded rod 22. Circular nut 24 can be used to meter the extrusion of a pre-determined amount of thermoplastic material by positioning it an appropriate distance from heft 14 and then advancing rod 14 until nut 24 meets heft 14. Thumb pad 26 is provided, of course, to receive thumb pressure to advance rod 22 and piston 16 as syringe 10 is held. Circular nut 24 can also be used to generate more force to advance rod 22 by positioning nut 24 against heft 22 and then turning nut 24 in the direction which advances rod 22, and therefore piston 16.

A wide range of materials can be used in fabricating the components of syringe 10 already described. It is preferred, however, that all of these components be fabricated from materials having relatively low thermal conductivity, such as those with a coefficient of thermal conductivity of below about 20 Btu/(hr)(ft$^2$)(°F./ft), to minimize heating of these components. In typical cases, barrel 12 might be constructed of stainless steel, glass or ceramics, heft 14 might be brass, and piston 16, rod 22, nut 24 and pad 26 might be constructed of stainless steel. Those skilled in the art will recognize, however, that many glass, ceramic, plastic, metal, or other materials will be suitable for each of these components.

A heater section for syringe 10 is positioned contiguous to barrel 12. The heater section has a tubular heater body 28 with raised flanges 30 and 32 at opposite sides thereof. Tubular heater body 28 has an inside diameter matching that of barrel 12. It is attached by an external thread on the part of body 28 extending beyond flange 30, which thread is matched to the internal thread at the terminal part of barrel 12. Heater body 28 is fabricated from a material having relatively good thermal conductivity, such as copper. As illustrated in FIG. 2, a washer 33, which can be formed from Teflon ® or other heat-insulating materials, is used as a heat barrier between heater body 28 and syringe barrel 12.

Electrical resistance heating wire 34 is wound around tubular heater body 28 between raised flanges 30 and 32. Nichrome or German silver wire is suitable. A thermally insulating sleeve 36 is then slipped over wire 34 to provide an outer covering at much lower temperatures. Although not illustrated, heating wire 34 can be provided with power from an internal power source, such as batteries, or from an external source, such as a transformer connected to an a-c outlet.

Hollow needle 38 is used to deliver extruded heated thermoplastic material into the cavity being filled. Typically, such needles useful in obturating root canal cavities have a needle gauge of from about 18 to about 30, and are about 1 inch or more in length. A convenient way to attach needle 38 is by using hub 40, which has an internal diameter matching that of syringe barrel 12 and also has an externally threaded portion which can be screwed tightly into flange 32 on heater body 28 thereby providing outstanding thermal contact therebetween. Needle 38 can be joined to hub 40 by swaging it into place and by using a silver braze which flows into any air space between needle 38 and hub 40; thus, excellent thermal contact is also achieved at this point.

Most commonly used materials, including most metals, are not sufficient for needle 38. Because it is an elongated tube which must be maintained at an elevated temperature along its entire length, only materials having a coefficient of thermal conductivity of greater than about 200 Btu/(hr)(ft$^2$)(°F./ft) are suitable. Silver is a particularly preferred material because of its high thermal conductivity and physiological inertness.

Syringe 10 is operated as follows. Piston 16 is withdrawn from barrel 12 by grasping heft 14 and pulling pad 26 rearwardly. Thermoplastic material, such as a stick of gutta-percha, is then inserted into barrel 12 after which piston 16 is reinserted and moved in the forward direction until it contacts the thermoplastic material. The power supply for heating wire 34 is then activated to heat the thermoplastic material within heater body 28. After a short time, heated thermoplastic material can be extruded from needle 38 by applying thumb pressure to pad 26 thereby advancing piston 16 in the forward direction. As previously mentioned, circular nut 24 can be used as a metering indicator or to assist in generating more force on piston 16 although this is usually not necessary. After the desired amount of thermoplastic material has been extruded, the power supply is inactivated.

A modified heater section is illustrated in FIG. 3. Therein, it can be seen that the heater is formed from a tubular body section 40, fabricated from a metal or other material having high thermal conductivity. Tubular body section 40 might be formed, for example, from copper or silver. A recessed area is provided for wrapping the tubular heater section with electrical resistance wire 42. Heat insulating tape 44, or other insulating material, is placed over electrical resistance wire 42 and a radiation shield 46, such as aluminum foil, is added. This heater section is also provided with internal threads suitable for attachment to the external threads of a syringe barrel at one end, and external threads suitable for mating with the internal threads of a needle hub at the other end.

An alternative embodiment of a syringe according to this invention, which is trigger operated, is illustrated in FIG. 4. Trigger-operated syringe 50 has an outer housing 52 which contains most of the components of syringe 50. Syringe 50 delivers extruded heated thermoplastic material in response to finger pressure on trigger lever 54. As trigger 54 is depressed, activator lever 55 closes microswitch 56 completing the circuit formed by contacts 58 and 60, respectively, contacting the terminals of batteries 62 and 64. Thus, electrical current flows to heater coil 66. As in prior embodiments, heating coil 66 is wrapped around a recessed area of tubular heater body 68. Heating coil 66 has a male electrical connector 70 which can be inserted into female electrical connector 72 mounted externally to barrel 74 of syringe 50. This provides a quick disconnect capability.

Depressing trigger lever 54 also simultaneously causes pawl rod 75 to advance thereby advancing ratchet rack 76 by means of spring-loaded pawl 78. Pawl 78 has a stop thereon, and after the stop is reached trigger lever 54 is released. Trigger spring 77 causes trigger 54 to return to its original position thereby allowing pawl 78 to open and re-engage gear rack 76 so that piston 80 can be advanced further by depressing trigger 54 once again. Rack 76 is integrally attached to piston rod 79 so that its movement is transmitted to piston 80, thereby extruding thermoplastic material through needle hub 82 and hollow needle 84.

Trigger-operated syringe 50 can be reloaded by depressing spring-loaded lock 86 to release pawl 78 from rack 76. This allows piston rod 78 to be withdrawn by simply pulling rearwardly on knob 88.

In addition to being driven by hand, the piston could also be driven mechanically, such as by a spring, or by a motor, pneumatically, hydraulically, or by other means.

Those skilled in the art will recognize many equivalents to the specific elements, components, materials and steps described herein. Such equivalents are intended to be covered by the following claims.

What is claimed is:

1. A method filling dental root canal cavities with thermoplastic material comprising the steps of:

providing a dental syringe having a chamber for holding a supply of thermoplastic material, a tubular needle, having a length of at least about one inch and an outer diameter within the range of diameters from that of an 18 gauge needle to that of a 30 gauge needle, fabricated from a material having high thermal conductivity of at least about 200 Btu/(hr.) (ft.$^2$)(°F./ft.), an electric heater for heating the thermoplastic material and a plunger for pushing softened thermoplastic material through the needle;

by means of the syringe heater, heating thermoplastic material within the syringe chamber and heating the needle to temperatures sufficient to soften the thermoplastic material and allow it to flow through the needle;

positioning the needle in a dental cavity;

pushing softened thermoplastic material through the needle into the dental cavity and thereby filling the cavity; and permitting the thermoplastic material within the dental cavity to cool and become a hardened mass.

* * * * *